United States Patent [19]

Foster et al.

[11] 4,041,129
[45] Aug. 9, 1977

[54] REMOVAL OF ACIDIC GASES FROM HYDROCARBON STREAMS

[75] Inventors: Raymond C. Foster, Boston; James J. Humphries, Jr., Wellesley, both of Mass.

[73] Assignee: Stone & Webster Engineering Corporation, Boston, Mass.

[21] Appl. No.: 490,935

[22] Filed: July 23, 1974

Related U.S. Application Data

[63] Continuation of Ser. No. 21,383, March 20, 1970, abandoned.

[51] Int. Cl.² .............................................. B01D 53/34
[52] U.S. Cl. .................................... 423/234; 423/245; 204/98; 204/104
[58] Field of Search ............... 423/210, 225, 234, 242, 423/220, 245, 226; 204/98, 104, 108 P

[56] References Cited

U.S. PATENT DOCUMENTS

| 1,132,697 | 3/1915 | Murray et al. | 423/242 |
|---|---|---|---|
| 2,497,954 | 2/1950 | McCulley | 423/229 |
| 3,344,050 | 9/1967 | Mayland et al. | 423/232 |
| 3,475,122 | 10/1969 | McRae et al. | 423/242 |
| 3,523,880 | 8/1970 | Parsi | 423/541 |
| 3,660,016 | 5/1972 | John et al. | 423/226 |
| 3,801,698 | 4/1974 | Lowrance et al. | 423/234 |

Primary Examiner—Earl C. Thomas
Attorney, Agent, or Firm—Morgan, Finnegan, Pine, Foley & Lee

[57] ABSTRACT

An apparatus and process for substantially reducing carbon dioxide and/or hydrogen sulfide levels in a hydrocarbon gas with simultaneous regeneration of reagent materials are disclosed. The process consists of passing the gas through an aqueous sodium hydroxide solution, reacting the effluent liquid with an acidic reagent, stripping the acidic gases therefrom and subjecting the resulting aqueous sodium sulfate solution to an electrolytic process. The apparatus used to carry out the process comprises an acidic gas absorbing unit, means for reacting the resulting effluent liquid, means for stripping the acidic gases and an electrolytic cell to convert soluble alkali metal salts into the corresponding alkali metal hydroxide and acidic reagents.

17 Claims, 2 Drawing Figures

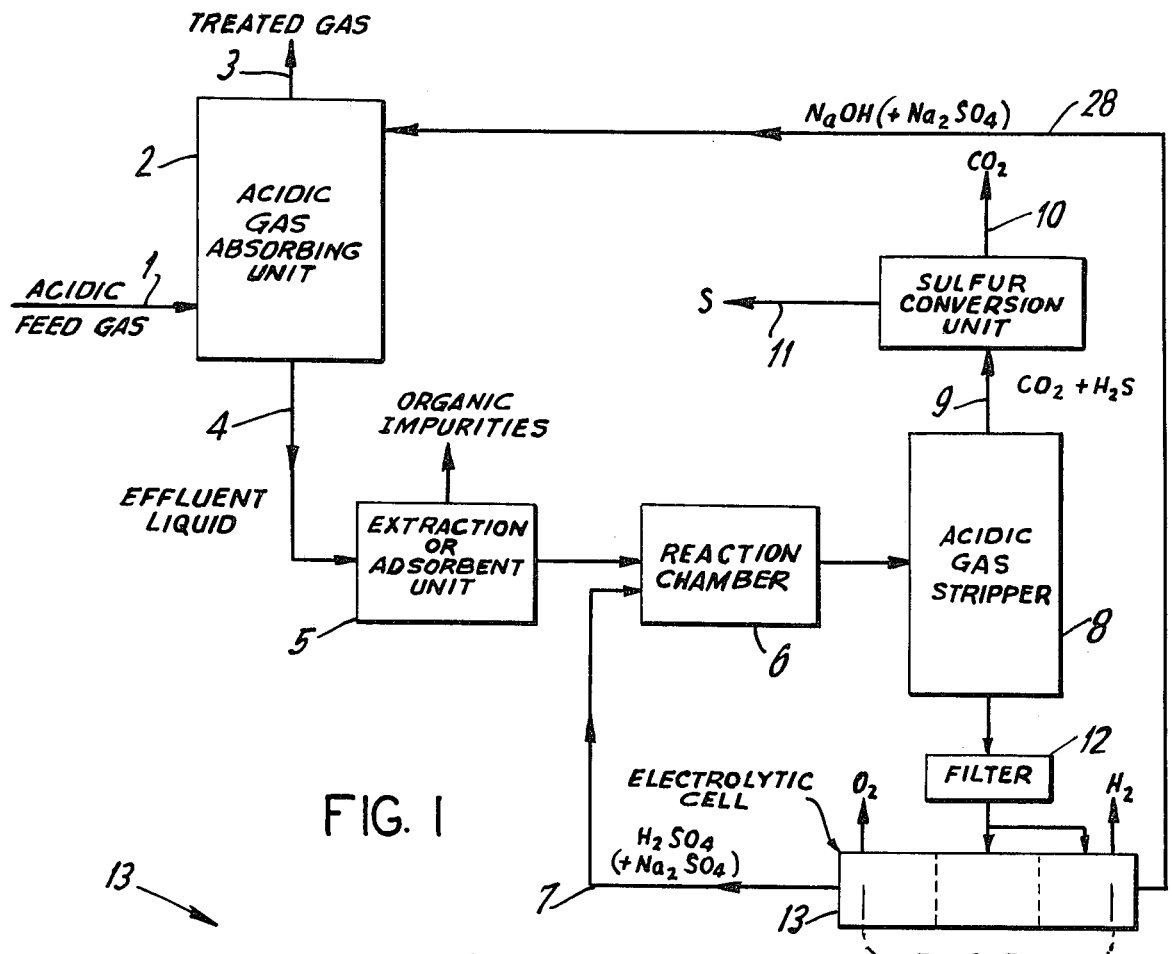
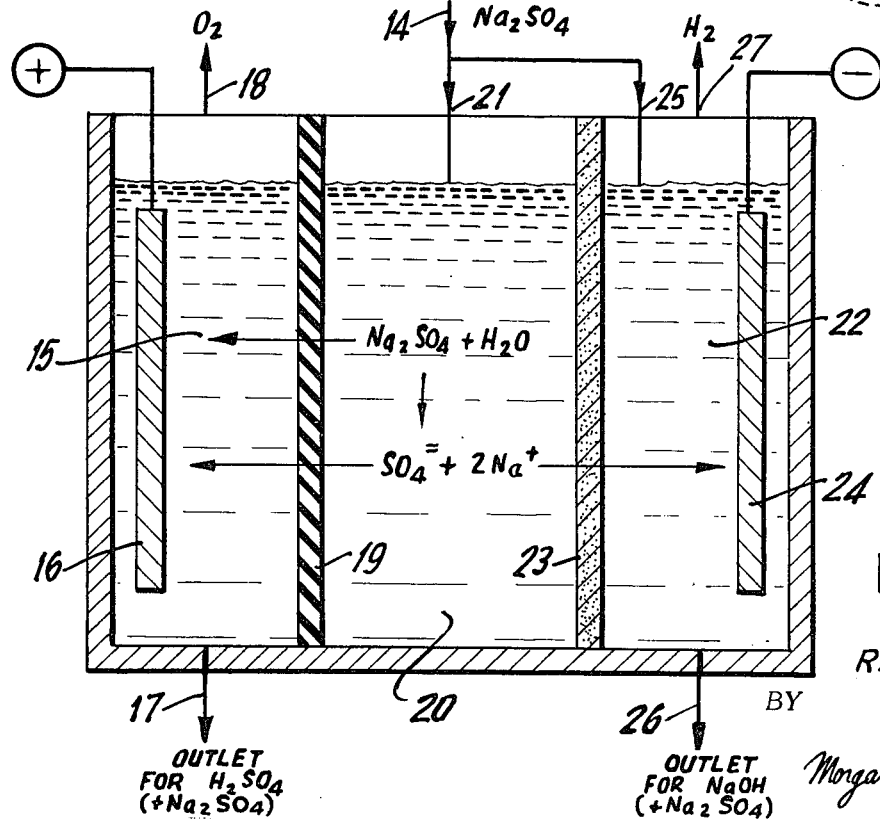

REMOVAL OF ACIDIC GASES FROM HYDROCARBON STREAMS

This is a continuation, of application Ser. No. 21,383, filed Mar. 20, 1970, and now abandoned.

BACKGROUND OF THE INVENTION

The invention relates to a process and apparatus for the removal of acidic gases such as carbon dioxide and hydrogen sulfide from a hydrocarbon gas. More particularly, it relates to a process for removing these acidic gas components and electrolytically converting the resulting aqueous sodium sulfate solution to sodium hydroxide and sulfuric acid products. These products can then be recycled to the appropriate stages in the inventive process for reuse. The sodium hydroxide is recycled to the sodium hydroxide treatment step and the sulfuric acid is recycled to the reaction step. The hydrogen sulfide can be converted to a usable sulfur product.

In the field of petroleum chemistry, it is highly desirable to remove acidic gases such as carbon dioxide and hydrogen sulfide from hydrocarbon gases which contain these materials generally in relatively small quantities. Illustrative of hydrocarbon gases which often contain these impurities are: gases obtained from the cracking of hydrocarbons such as gas oil, naphtha, ethane, etc. Frequently, naturally occuring hydrocarbons, such as natural gas, contain these undesirable materials. Their undesirablility derives in part from the fact that their acidic nature is prominent under aqueous conditions. This acidic quality can also be detrimental when using the particular gas for its intended use. For instance, they impart corrosive properties and, in the case of hydrogen sulfide, toxic properties. Also, in many instances the presence of these acid gases in hydrocarbon streams is detrimental to subsequent processing of these streams and to the manufacture of chemicals therefrom.

The removal of these unwanted components from a hydrocarbon gas is generally accomplished by scrubbing the gas in a suitable tower with a water solution of a reagent capable of reacting with the acidic gases. Potassium carbonate is frequently used. For example, it reacts with carbon dioxide to form potassium bicarbonate in solution, which may be regenerated by driving off the excess carbon dioxide and either venting it or collecting it for some other usage. However, potassium carbonate is effective for the removal of hydrogen sulfide only in special cases.

Among others, one type of solution frequently employed for scrubbing the gases is a solution containing monoethanolamine. Such a solution can also be regenerated. However, it has three principal drawbacks: relatively high vapor pressure; the fact that it reacts essentially irreversibly with carbonyl sulfide (a common constituent of gas from cracking operations) with resultant substantial loss of the amine; and that it is generally imprasticable to remove substantially all the acidic gases using this solvent.

Still another solution which has been used effectively is aqueous sodium hydroxide. This reagent is capable of removing substantially all the acid constituents from gases such as cracked gases and natural gases. Use of this solution, however, suffers from the notable disadvantages that the expensive sodium hydroxide is consumed, it is not recovered, and moreover the waste products from the scrubbing system constitute a potentially serious source of water pollution.

Various removal systems have been devised which are capable of removing these gaseous constituents to various final levels in the treated gases. However, no method has been devised until the present time for substantially complete removal of hydrogen sulfide and/or carbon dioxide from a hydrocarbon gas whereby there is simultaneous stripping of said gases and conversion of $H_2S$ to useful sulfur with efficient andd economic regeneration of reagent materials in condition suitable for recycling purposes. It is the general purpose of the present invention to provide a process and apparatus for attaining these ends.

SUMMARY OF THE INVENTION

This invention relates to a novel process and apparatus in which acidic gases such as carbon dioxide and/or hydrogen sulfide are substantially reduced in a hydrocarbon gas with simultaneous regeneration of reagent material. The process comprises: (a) passing said gas through an aqueous sodium hydroxide solution: (b) reacting the resulting effluent liquid with aqueous sulfuric acid or an aqueous mixture containing sulfuric acid and sodium sulfate in amounts sufficient to liberate acidic gases such as hydrogen sulfide and carbon dioxide: (c) removing said acidic gases by a stripping operation; and (d) subjecting the resulting aqueous sodium sulfate solution to an electrolytic process whereby an aqueous solution of sulfuric acid or an aqueous mixture of sulfuric acid and sodium sulfate is collected at the anode and is recycled for utilization in said reaction step and whereby aqueous sodium hydroxide is formed at the cathode and is recycled, optionally admixed with sodium sulfate, for use in the sodium hydroxide treatment step.

Also disclosed and claimed herein is the apparatus which is utilized to carry out the aforesaid inventive process. The apparatus comprises: (a) an acidic gas absorbing unit having aqueous sodium hydroxide therein: (b) means for reacting the effluent liquid from the acidic gas absorbing unit: (c) means for stripping the acidic gases from the reacted effluent liquid; and (d) an electrolytic cell for receiving the stripped reacted liquid to convert soluble alkali metal salts into the corresponding alkali metal hydroxides and acids.

The last step, the electrolytic conversion, more specifically entails the conversion of a sodium sulfate solution to sodium hydroxide and sulfuric acid. It is the cornerstone of the entire inventive process for it results in the formation of essential reagents offsetting the cost of the regenerating system.

For purposes of this invention, an acidic gas is either hydrogen sulfide, carbon dioxide, carbonyl sulfide which can be reacted with water to form hydrogen sulfide and carbon dioxide, low molecular weight mercaptans or mixtures thereof. These acidic materials are frequently found in hydrocarbon gases. For example, they may be found in refinery gases, natural gases and cracked gases. Accordingly, the present invention contemplates the removal of these materials from any hydrocarbon gas which contains these components. The herein disclosed process is found to be particularly effective in removal of acidic gases from gases formed from cracking hydrocarbons such as gas oils, naphthas and ethane as well as from naturally occuring hydrocarbons which contain these acidic materials.

The first treatment or step in the presently disclosed process deals with an aqueous sodium hydroxide contact procedure. This is generally effected using well-known techniques familiar to those skilled in this particular art. For instance, a gas which has been obtained from the cracking of gas oil and which has been compressed to about 15 atmospheres above atmospheric pressure is passed through a container or tower which contains a solution of aqueous sodium hydroxide. The preferred method is to have the gas come in contact with the sodium hydroxide solution in a substantially countercurrent manner. The gas is passed from the contacting device and may be further processed. The gas so treated is substantially free of any carbon dioxide or hydrogen sulfide. The amount of the sodium hydroxide solution is not critical, the only requirement being that it is present in sufficient amounts to react with the acid gases present. The acidic gases $CO_2$ and $H_2S$ will be converted to sodium carbonate and sodium sulfide, respectively, and possibly also in part to sodium bisulfide and sodium bicarbonate. If low molecular weight mercaptans are present, they can be reacted under appropriate conditions to form the corresponding sodium mercaptides. It is possible to use an excess amount of sodium hydroxide in relation to the gas to be treated; however, it will be undesirable since such an excess of sodium hydroxide is more costly, will have direct bearing on the amount of reacting agent used in the subsequent treatment and will make necessary a large electrolytic conversion step. For these reasons, it is desirable to use the least amount of sodium hydroxide which is required to remove the hydrogen sulfide and carbon dioxide from the gas. From a practical point of view, a small excess of sodium hydroxide will most likely be present.

This slight excess of sodium hydroxide will tend to preclude the formation of sodium bisulfide and sodium bicarbonate. Alternatively, if no excess is present, then theoretically sodium bisulfide and sodium bicarbonate could be produced along with sodium sulfide and sodium carbonate.

The above-described chemical reactions can be shown by the following chemical equations:

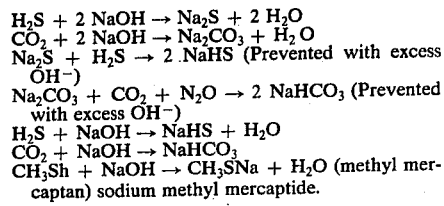

At this stage of the herein disclosed novel process, one has an aqueous solution containing sodium carbonate and sodium sulfide and possibly, in addition, sodium bisulfide and sodium bicarbonate. It is, of course, apparent that these substances in the aqueous phase exist in the ionic form.

The next step is the reacting of the solution containing the above constituents. Its purpose is to convert the sodium sulfide and sodium bisulfide (if present) to sodium sulfate and hydrogen sulfide. The $H_2S$ gas formed in situ is easily removed from the solution by a stripping operation. The reaction also relates to the reaction which occurs between sodium carbonate and sodium bicarbonate, if present, and sulfuic acid to yield sodium sulfate and carbon dioxide. Carbon dioxide being a gas is likewise easily removed by a stripping operation. Any low molecular weight sodium mercaptide which may be present is converted to sodium sulfate and the corresponding mercaptan which because of its low molecular weight can be removed by stripping. The actual stripping operation is effected in the acidic gas stripper chamber wherein the gaseous components consisting of carbon dioxide and hydrogen sulfide are stripped under moderate to low pressure. A particularly desirable embodiment of this invention relates to a procedure whereby $H_2S$ which is stripped from solution is converted to free sulfur, a valuable chemical raw material.

The chemical reactions which take place during the reaction step can be shown by the following equations:

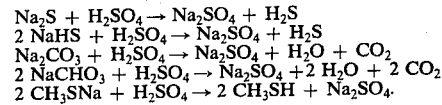

The final step is concerned with an electrolytic conversion in which the resulting aqueous sodium sulfate solution stripped free of the acidic components is optionally filtered and then subjected to an electrolytic process. The electrolytic method converts the aqueous sodium sulfate solution to the corresponding hydroxide; namely, sodium hydroxide and to the corresponding acid, sulfuric acid. The process utilized may be essentially the same as that described in Tirell et al. U.S. Pat. No. 3,135,673 which employs a cell having three compartments containing an ion-exchange membrane selectively permeable to cations defining the cation compartment and a spaced acid-resistance hydraulically permeable diaphragm defining the anode chamber. To the center compartment is passed the salt solution. Deionized water or other solutions are passed into the cathode compartment and an electric current is impressed upon the cell causing migration of cations of the electrolyte through the cation permselective membrane into the cathode compartment where combination with hydroxyl ions produced by the electrolysis of water at the cathode yields the corresponding metal hydroxide. Anions and to a lesser extent cations to the electrolyte pass through the hydraulically permeable diaphram into the anode compartment where combination with hydrogen ions produced by the elctrolysis of water at the anode produces the corresponding acid which is admixed with the salt fed to the cell.

The present invention is not limited to the use of the three-compartment cell described in the preceding paragraph. A two-compartment cell of the type described in Mayland et al., U.S. Pat. No. 3,485,743, may be used and there are numerous other electrolytic cells which are applicable in the practice of this invention. It must be understood that the constituents in and compositions of the various circulating streams are dependent on the characteristics of the particullar electrolytic cell and on the reagents employed. Other changes in the cyclical flow of the fluids within the system may be called for depending on the nature of the electrolytic cell but these changes will be apparent to anyone skilled in the art.

DESCRIPTION OF THE DRAWINGS

The inventior will be described with reference to the accompanying drawings which will give a clearer understanding of the invention and preferred method of practicing the invention.

FIG. 1 is a flow sheet depicting the overall cyclic process in a sequential manner and FIG. 2 is a schematic diagram of the electrolytic cell system of the invention.

DESCRPTION OF THE PREFERRED EMBODIMENT

The flow sheet shown in FIG. 1 is the preferred embodiment of the invention. The cyclic process contemplates the treatment of a hydrocarbon gas containing acidic gases with a caustic solution, reaction of the resulting effluent liquid, removal of hydrogen sulfide and carbon dioxide by a stripping operation, regeneration of reagents by means of an electrolytic process and production of sulfur from the hydrogen sulfide.

In general, the apparatus includes an acidic gas absorbing unit, means for substantially removing organic impurities from the effluent liquid withdrawn from the absorbing unit, a reaction chamber which may be simply a section of pipe line, an acidic gas stripping unit and an electrolytic cell. For purposes of clarity and simplicity, heat exchange apparatus and pumps are not shown in FIG. 1 or described in this specification but their use will be obvious to those skilled in the art.

Referring now to FIG. 1, which is diagramatically illustrative of a simplified system suitablle for substantially reducing hydrogen sulfide and carbon dioxide levels from a hydrocarbon gas such as that obtained from hydrocarbon cracking units or naturally occurring hydrocarbons which contain these substances, the process gas 1 is delivered to the acidic gas absorbing unit 2. This unit is preferably a scrubbing tower in which the aqueous sodium hydroxide and sodium sulfate contained therein is contacted with the acidic feed gas countercurrently. In this manner, the feed gas is assured of intimate mixing with the absorber solution of aqueous sodium hydroxide and sodium sulfate. The scrubbed or treated gas 3 which is substantially free of acidic gas components is piped from the absorber for subsequent transportation or processing.

The spent effluent liquid 4 coming from the acidic gas absorbing unit is collected at the bottom of the tower and is carried by a conduit to the extraction or adsorbent unit 5. At this stage, the effluent liquid which contains sodium sulfide and sodium carbonate, and possibly sodium bisulfide and sodium bicarbonate is subjected to either an extraction step or an adsorbent treatment in order to remmove any organic impurities which may be present. If an extraction technique is used, a water-immisible organic solvent is admixed intimately with the aqueous effluent liquid in an extractor and then allowed to separate. The organic phase which comprises the organic solvent and impurities therein is then removed by separation.

The preferred organic solvent for this technique is a hydrocarbon having a boiling point no higher than that of a gas oil. For example, applicable solvents of this type include naphthas and gas oils. However, other fractions having boiling points within or below the range described above are also contemplated.

The removal of organic impurities can also be effected by an adsorbent treatment. For instance, the aqueous solution can be passed through a bed of adsorbent material such as carbon, charcoal, clay or silica.

The effluent liquid can now be reacted with an acid, preferably sulfuric acid, in a reaction chamber 6 or section of pipe between the point of admixture of the two liquid streams and the acidic gas stripper. The sulfuric acid for this puspose (mixed with sodium sulfate) 7 is carried by a condiut from the electrolytic cell to a point just prior to the receipt by the reaction chamber of the effluent liquid. The reaction chamber, therefore, receives an aqueous mixture of sulfuric acid which contains some sodium sulfate and the effluent liquid which comprises sodium sulfide, sodium carbonate and possibly sodium bisulfide and sodium bicarbonate as well.

The chemical reactions which occur in the reaction chamber have been shown earilet and relate to the production of hydrogen sulfide from the sodium sulfide and sodium bisulfide constituents while carbon dioxide is formed from the sodium carbonate and sodium bicarbonate components Both gases form in situ as the reaction takes place. The resulting mixture is then transferred by conduit to the acidic gas stripper 8. Under proper condition such as moderate or low pressures and/or the application of heat, the gaseous components $CO_2$ and $H_2S$ 9 are stripped from the solution and may be vented to the atmosphere 10. A preferred embodiment of the instant invention, however, concerns the subsequent treatment of the stripped acidic gases to convert the $H_2S$ to a salable product; namely, sulfur 11. Accordingly, there results the formation of a commercially desirable product from an undesirable component present as an impurity in the original gas feed.

The aqueous solution which remains after the stripping procedure is essentially a sodium sulfate solution. It is collected at the bottom of the acidic gas stripper and is carried by conduit to the electrolytic cell 13 in order to effect the last step of the cyclic process. Prior to the elctrolytic conversion step, and sodium sulfate solution can be filtered using an ordinary filtering apparatus 12. In many instances, a filtering step will be unnecessary. However, to insure minimal contamination in the electrolytic cell, it is generally advisable.

The sodium sulfate solution 14 is transferred through a conduit to the center compartment of a three-compartment electrolytic cell. A suitable construction for the electrolytic cell is described in FIG. 2. It contains an anode compartment 15 which has an acid resistant anode 16 and is provided with an outlet 17 for the anolyte effluent product, a solution of sulfuric acid and sodium sulfate, and an outlet 18 for the gaseous anode product, oxygen. The anode compartment 15 is separated from the center compartment by means of an acid resistant hydraulically permeable non-permselective diaphram 19. The center compartment 20 contains an inlet 21 through which the sodium sulfate solution is introduced. The cathode compartment 22 is separated from the center compartment 20 by a cation-exchange membrane 23 selectively permeable to cations. The cathode compartment 22 is provided with a cathode 24 and an inlet 25 through which a portion of the sodium sulfate solution is added. In pace of sodium sulfate, water alone can be used. However, in order to prevent dilution of the circulating solutions, it is more preferred to use sodium sulfate. It is obvious that, if one adds sodium sulfate to the cathode compartment, the sodium hydroxide which is collected is admixed with a sodium sulfate solution. An outlet in the cathode compartment serves to withdraw the catholyte effluent product sodium hydroxide 26. Another outlet 27 which appears at the top of the cathode compartment 22 serves as an exit pipe for withdrawal of the gaseous cathodic product, hydrogen.

In the operation of this electrolytic process, a concentrated sodium sulfate solution is introduced into the cell through inlet 21 at a rate and pressure sufficiently high so that the passage of said sodium sulfate through the porous diaphram is at a rate sufficiently rapid to substantially curtail the migration of hydrogen ions from the anode toward the cathode.

Simultaneously, sodium sulfate solution or water is passed into the cathode compartment at a rate corresponding to the concentration of sodium hydroxide desired in the cathode effluent product, and a direct electric current is impressed upon the cell. The cationic constituents, for example, sodium ions, pass through the cation-exchange membrane into the cathode compartment where combination with hydroxyl ions produced at the cathode by the electrolysis of water results in the formation of sodium hydroxide which may then be withdrawn from the cathode compartment. The sodium sulate in the center compartment now having been partially depleted of its sodium ions passes through the diaphram into the anode compartment where combination of the sulfate anions with hydrogen ions produced by electrolysis of water at the anode provides sulfuric acid which is withdrawn together with unreacted sodium sulfate at the provided outlet. Generally, the sulfuric acid solution will contain about equal concentrations of sulfuric acid and sodium sulfate.

The reagent materials required for the earlier stages in the process are now regenerated and can be carried by conduits to the appropriate locations in the cyclic process. For instance, the sodium hydroxide which may contain some sodium sulfate 28 is transferred to the acid gas absorbing unit for further treatment of acidic feed gas. The sulfuric acid solution containing sodium sulfate 7 is returned to mix with and react with the liquid from the absorber which has been treated to remove organic impurities. It may be returned directly to the reaction chamber or may be placed in the line with the effluent liquid and the mixture subsequently carried to the reaction chamber.

The invention in it broader aspects is not limited to the specific steps, methods, compositions and improvements shown and described herein, but departures may be made within the scope of the accompanying claims without departing from the principles of the invention.

What is claimed is:

1. In a cyclic process for substantially reducing the carbon dioxide and/or hydrogen sulfide content present as acidic gases in a gas obtained from the cracking of a hydrocarbon selected from the group consisting of gas oil, naphtha and ethane, and said gas further containing undesirable organic impurities therein, with simultaneous regeneration of reagent materials which comprises:
   a. passing the cracked gas containing the acidic gases through an aqueous sodium hydroxide solution and obtaining an effluent containing the undesirable organic impurities and said acidic gases in converted form;
   b. reacting said effluent liquid with aqueous sulfuric acid or an aqueous mixture containing sulfuric acid and sodium sulfate in an amount sufficient to substantially liberate the converted acidic gases consisting essentially of hydrogen sulfide and/or carbon dioxide that may be present therein;
   c. subjecting said treated effluent liquid to a stripping operation to remove any liberated gases therefrom and thereby leaving an aqueous sodium sulfate containing solution; and
   d. subjecting said resulting aqueous sodium sulfate containing solution to an electrolytic process treatment whereby aqueous sulfuric acid or an aqueous mixture of sulfuric acid and sodium sulfate is collected at the anode and is recycled for utilization in the aforesaid reaction step and aqueous sodium hydroxide which forms at the cathode is collected and recycled for use in the sodium hydroxide treatment step, the improvement which comprises treating the effluent from the alkali metal hydroxide treatment of step (a) to remove substantially all organic impurities therefrom.

2. The process according to claim 1 wherein said aqueous sodium hydroxide solution contains sodium sulfate.

3. The process according to claim 1 wherein said sodium hydroxide which forms at the cathode contains sodium sulfate.

4. The process according to claim 1 wherein to the cathode compartment involved in the electrolytic process is added aqueous sodium sulfate in an amount sufficient to maintain the electrolytic membrane free from solids.

5. The process according to claim 1 wherein said effluent liquid contains a small amount of sodium hydroxide.

6. The process according to claim 1 wherein said effluent liquid contains sodium bisulfide and/or sodium bicarbonate.

7. The process according to claim 1 wherein the effluent liquid from sodium hydroxide contacting is extracted with a substantially water-immiscible organic solvent.

8. The process according to claim 7 wherein said organic solvent is a hydrocarbon having a boiling point no higher than that of a gas oil.

9. The process according to claim 8 wherein said hydrocarbon solvent is a naphtha.

10. The process according to claim 8 wherein said hydrocarbon solvent is a gas oil.

11. The process according to claim 1 wherein said effluent liquid from sodium hdroxide contacting is contacted with an adsorbent.

12. The process according to claim 1 wherein said sodium hydroxide treatment step consists of contacting said gas substantially countercurrently with said sodium hydroxide solution.

13. The process according to claim 1 wherein the liberated gases from the stripping operation include hydrogen sulfide which is converted to sulfur.

14. The process according to claim 1 wherein the aqueous sodium sulfate from the stripping operation is filtered before it is subjected to the electrolytic process.

15. The process according to claim 1 wherein said electrolytic process is carried out in an electrolytic cell capable of converting soluble alkali metal salts into their corresponding alkali metal hydroxides and acids.

16. The process according to claim 15 wherein said soluble alkali metal salt is sodium sulfate which is converted to sodium hydroxide and sulfuric acid.

17. The process according to claim 15 wherein said electrolytic cell is a three compartment cell comprising a cathode compartment, a center compartment and an anode compartment, the cathode compartment being separated from the center compartment by a cation selective ion exchange membrane and the center compartment being separated from the anode compartment by a fluid-permeable diaphram.

* * * * *